(12) United States Patent
Catt et al.

(10) Patent No.: US 7,044,919 B1
(45) Date of Patent: May 16, 2006

(54) TEST METHODS, DEVICES AND TEST KITS

(76) Inventors: Michael Catt, c/o Unipath Ltd, Priory Business Park, Bedford (GB), MK44 3UP; Rosie L Habeshaw, c/o Unipath Ltd, Priory Business Park, Bedford (GB), MK33 3UP; Keith May, c/o Unipath Ltd, Priory Business Park, Bedford (GB), MK44 3UP; Fiona McNae, Ground Floor Flat, 16B Osward Road, London (GB), SW17 7SS; Andrew P Phelan, c/o Unipath Ltd, Priory Business Park, Bedford (GB), MK44 3UP (*) Notice: Subject to any disclaimer, the term of this patent is extended or adjusted under 35 U.S.C. 154(b) by 0 days.

(21) Appl. No.: 09/285,060

(22) Filed: Apr. 2, 1999

(30) Foreign Application Priority Data

Apr. 2, 1998 (GB) ............................................. 9807134

(51) Int. Cl.
*A61B 10/00* (2006.01)

(52) U.S. Cl. .......................................... 600/551; 436/65
(58) Field of Classification Search ................. 600/551; 436/65
See application file for complete search history.

(56) References Cited

U.S. PATENT DOCUMENTS

| | | | |
|---|---|---|---|
| 3,141,740 A | 7/1964 | Wild | 436/65 |
| 3,406,015 A | 10/1968 | Foster | 435/28 |
| 3,406,016 A | 10/1968 | Foster et al. | 435/28 |
| 3,434,801 A | 3/1969 | Scherr | 422/56 |
| 3,436,186 A | 4/1969 | Mcsweeney et al. | 436/65 |
| 3,749,089 A | 7/1973 | Derr | 600/345 |
| 3,875,013 A | 4/1975 | Manautou et al. | 435/18 |
| 3,924,609 A | 12/1975 | Friedenberg et al. | 600/551 |
| 3,926,037 A | 12/1975 | Kopito et al. | 73/54.37 |
| 3,968,011 A | 7/1976 | Manautou et al. | 435/18 |
| 3,986,494 A | 10/1976 | Preti et al. | 600/551 |
| 3,991,174 A | 11/1976 | Grundman | 436/521 |
| 4,002,056 A | 1/1977 | Kopito et al. | 73/54.37 |
| 4,010,738 A | 3/1977 | Preti et al. | 600/551 |
| 4,013,066 A | 3/1977 | Schuster | 600/551 |
| 4,031,365 A | 6/1977 | Raggiotti et al. | 702/131 |
| 4,036,212 A | 7/1977 | Karuhn | 600/551 |
| 4,059,986 A | 11/1977 | Schuster | 73/54.37 |
| 4,072,045 A | 2/1978 | Kopito | 73/54.37 |
| 4,119,089 A | 10/1978 | Preti et al. | 436/65 |
| 4,123,510 A | 10/1978 | Banik et al. | 436/520 |
| 4,148,304 A | 4/1979 | Mull | 600/549 |
| 4,151,831 A | 5/1979 | Lester | 600/549 |

(Continued)

FOREIGN PATENT DOCUMENTS

| | | |
|---|---|---|
| EP | 0703454 | 3/1996 |
| EP | 0754949 | 1/1997 |
| EP | 0833160 | 4/1998 |
| WO | 95 01128 | 1/1995 |
| WO | 95 13543 | 5/1995 |

*Primary Examiner*—Robert L. Nasser
*Assistant Examiner*—Charles Marmor, II

(57) ABSTRACT

A method for determining the time of maximum fertility in the mammalian ovulation cycle, for the purpose of assisting conception, wherein testing is conducted over a period of days in the current ovulation cycle on samples of body fluid obtained from an individual human subject to detect an elevated concentration of first analyte, such as luteinising hormone (LH) indicative of the event of ovulation, and additionally testing is conducted over a period of days in the current ovulation cycle on samples of body fluid obtained from the individual subject to detect an elevated concentration of a second analyte, such as estradiol or a metabolite thereof, especially estradiol-3-glucuronide (E3G), to provide advance warning of ovulation.

49 Claims, 7 Drawing Sheets

U.S. PATENT DOCUMENTS

| | | | |
|---|---|---|---|
| 4,151,833 A | 5/1979 | Polishuk | 600/551 |
| 4,208,187 A | 6/1980 | Givner | 436/521 |
| 4,232,215 A | 11/1980 | Hanley | 235/78 RC |
| 4,246,907 A | 1/1981 | Bullock | 600/551 |
| 4,261,371 A | 4/1981 | Reading, III | 600/551 |
| 4,312,360 A | 1/1982 | Conway et al. | 600/549 |
| 4,367,527 A | 1/1983 | Desjacques | 368/107 |
| 4,370,727 A | 1/1983 | Bellet | 708/105 |
| 4,377,171 A | 3/1983 | Wada | 600/549 |
| 4,381,121 A | 4/1983 | Hanley | 283/115 |
| 4,385,125 A | 5/1983 | Preti et al. | 436/65 |
| 4,396,020 A | 8/1983 | Wolff et al. | 600/551 |
| 4,408,905 A | 10/1983 | Ehrenkranz | 374/157 |
| 4,443,851 A | 4/1984 | Lin | 600/551 |
| 4,450,239 A | 5/1984 | Chatterton | 435/7.92 |
| 4,465,077 A | 8/1984 | Schneider | 600/551 |
| 4,466,445 A | 8/1984 | Abrams | 600/549 |
| 4,475,158 A | 10/1984 | Elias | 600/549 |
| 4,488,560 A | 12/1984 | Takamura | 600/551 |
| 4,498,481 A | 2/1985 | Lemke | 600/547 |
| 4,530,366 A | 7/1985 | Nessi et al. | 600/549 |
| 4,534,362 A | 8/1985 | Schumacher et al. | 600/551 |
| 4,557,273 A | 12/1985 | Stoller et al. | 600/551 |
| 4,614,715 A | 9/1986 | Tsibris et al. | 435/28 |
| 4,670,401 A | 6/1987 | Cutler et al. | 436/65 |
| 4,676,254 A | 6/1987 | Frohn | 600/549 |
| 4,685,471 A | 8/1987 | Regas et al. | 600/547 |
| 4,691,714 A | 9/1987 | Wong et al. | 600/551 |
| 4,752,880 A | 6/1988 | Aeschlimann | 600/551 |
| 4,753,247 A | 6/1988 | Kirsner | 600/547 |
| 4,770,186 A * | 9/1988 | Regas et al. | 600/551 |
| 4,779,627 A | 10/1988 | Kosasky | 600/551 |
| 4,921,808 A | 5/1990 | Schneyer et al. | 436/503 |
| 4,931,403 A * | 6/1990 | Cutler et al. | 600/551 |
| 5,043,888 A | 8/1991 | Uriarte | 600/551 |
| 5,050,612 A | 9/1991 | Matsumura | 600/483 |
| 5,063,903 A | 11/1991 | Wahl et al. | 123/500 |
| 5,091,170 A | 2/1992 | Navot | 436/65 |
| 5,137,028 A | 8/1992 | Nishimura | 600/551 |
| 5,209,238 A | 5/1993 | Sundhar | 600/551 |
| 5,216,599 A | 6/1993 | Uebe et al. | 600/551 |
| 5,248,593 A | 9/1993 | Hubner-Parajsz et al. | 435/7.9 |
| 5,467,778 A * | 11/1995 | Catt et al. | 600/551 |
| 5,657,762 A * | 8/1997 | Coley et al. | 600/551 |
| 5,685,319 A * | 11/1997 | Marett | 600/551 |
| 5,721,142 A * | 2/1998 | Klemm et al. | 600/551 |
| 5,881,673 A * | 3/1999 | Beach et al. | 600/551 |

* cited by examiner

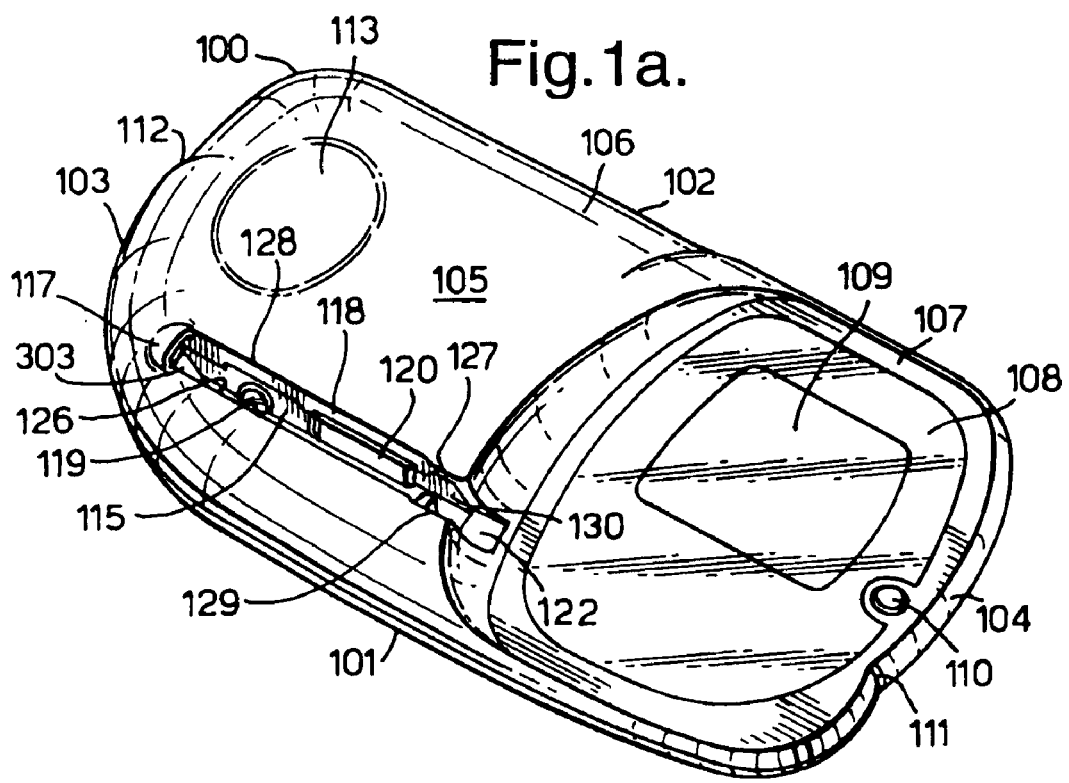
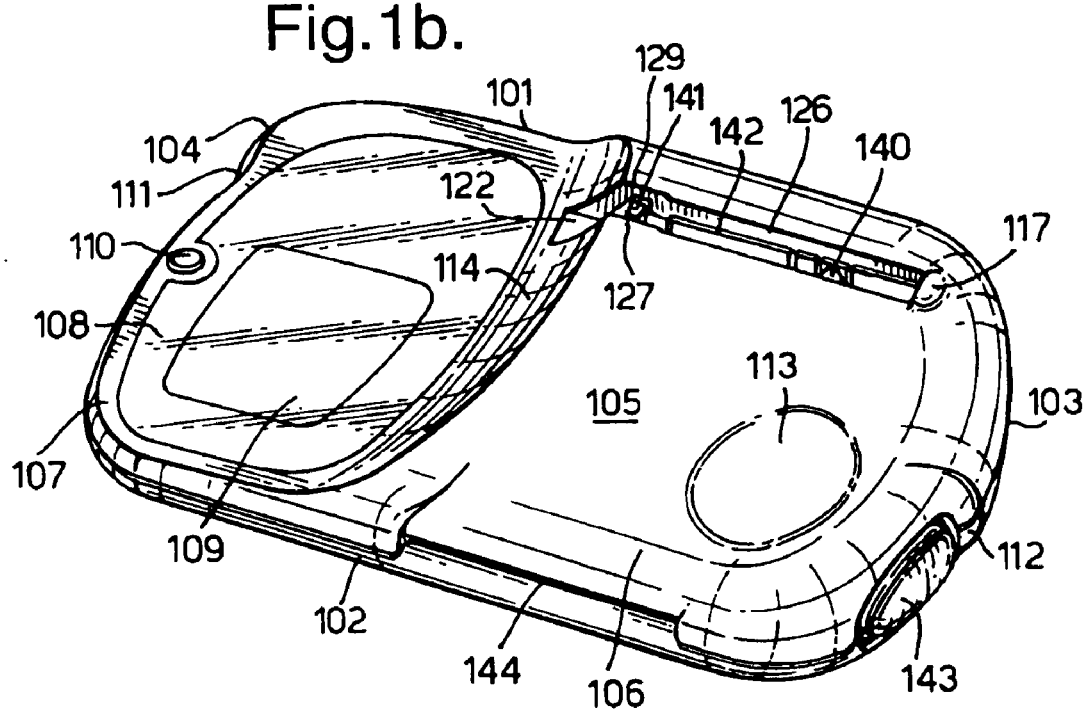

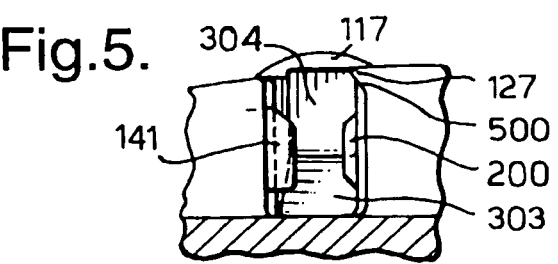
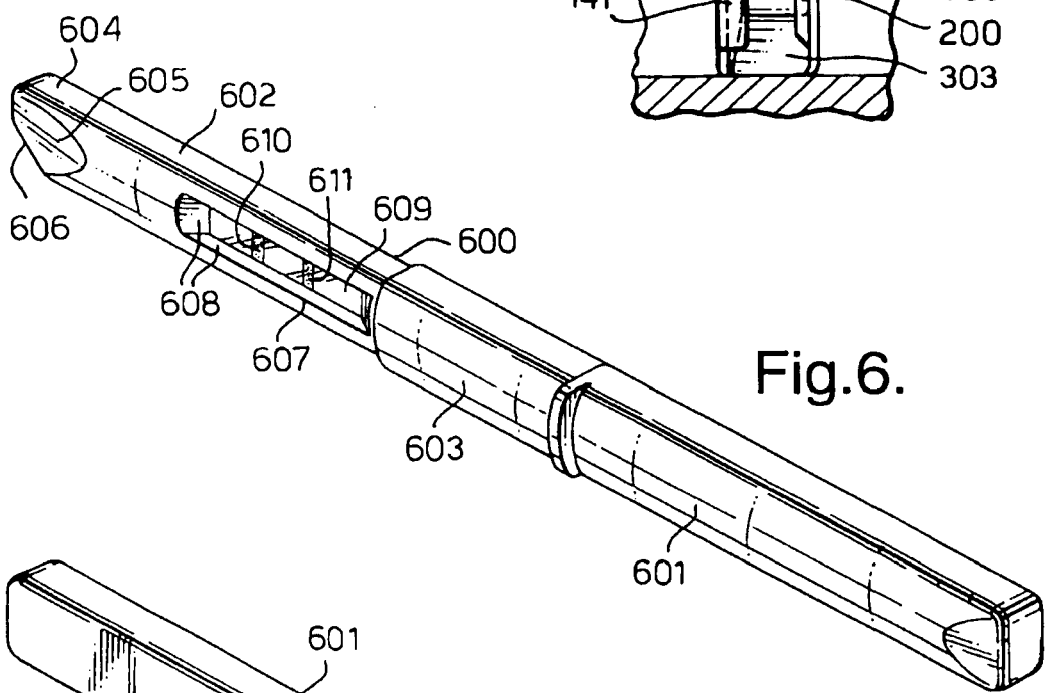
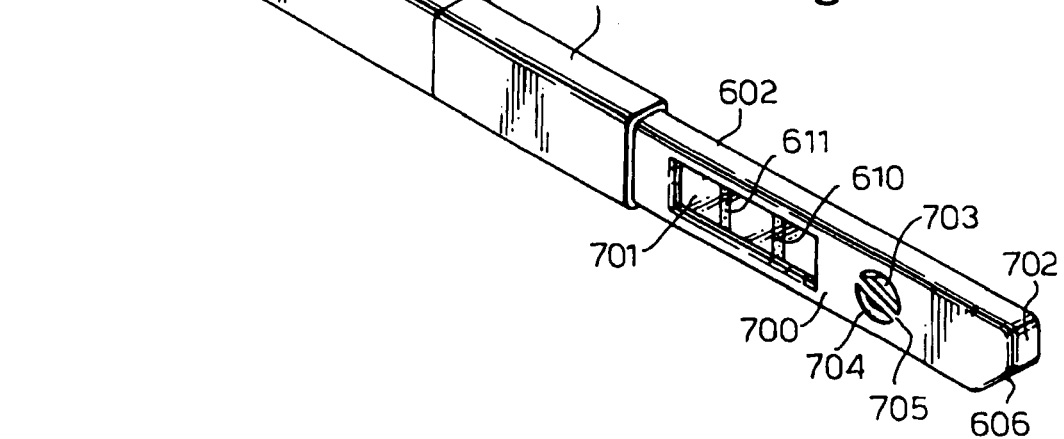

TEST METHODS, DEVICES AND TEST KITS

FIELD OF THE INVENTION

This invention relates to test methods, and also to devices and test kits for use in such methods, for determining the time of maximum fertility in the mammalian ovulation cycle.

BACKGROUND OF THE INVENTION

Devices are already available commercially to test the concentration of luteinizing hormone (LH) in human urine. Typically these devices provide a coloured signal readable by eye, the intensity of which alters with increasing LH concentration. Examples are described in EP-A-291194 and EP-A-383619. A series of regular tests, for example daily tests, are conducted during the cycle to pinpoint the LH surge or LH peak that is associated with the event of ovulation. This information is used to assist conception. It indicates the brief time in the ovulation cycle during which natural insemination is most likely to result in pregnancy. The information is also useful to health professionals conducting IVF treatments.

Although the existing tests make a valuable contribution in this area, the essentially transient nature of this physiological indicator can cause the ovulation event to be missed.

Moreover, at least in some individuals, comparatively high LH concentrations may be observed at times in the cycle not associated with the event of ovulation. This may occur for example due to gross variations in urine concentration. High LH concentrations arising from such causes can be wrongly associated with the event of ovulation.

Accordingly there is a need for improved test methods and test kits that enable ovulation to be pinpointed more accurately and for the likelihood of false indications to be reduced.

Ways of monitoring the mammalian ovulation cycle, primarily for the purpose of contraception, using analytes such as LH and estrone-3-glucuronide (E3G) are described in EP-A-656118, EP-A-656119 and EP-A-656120.

It has previously been proposed to use E3G (also in conjunction with LH) as an indicator of fertility status primarily for the purposes of contraception, although such information can also be used to assist conception if desired. In WO 95/01128 a base line E3G level is established at the start of an ovulation cycle and used as a reference against which to compare subsequent E3G signals to detect a rise indicative of the commencement of the fertile phase. For the avoidance of conception an adequately early warning of the onset of the fertile phase must be given, and an E3G rise associated with that onset will be much lower than is desirable for the purposes of the present invention. In the present invention, the objective is to pin-point as accurately as possible the time of maximum fertility. Accordingly, the optimum ratio between an E3G test signal and the base line signal in the present context would be quite inappropriate for the purposes of contraception.

GENERAL DESCRIPTION OF THE INVENTION

According to one aspect of the invention, a more reliable identification of the event of ovulation can be achieved if, in addition to the measurement of the concentration of a first analyte (such as LH) that pin-points the events of ovulation, a further body fluid analyte is also measured. This further analyte should be one for which the body fluid concentration alters significantly in advance of the ovulation event. This provides warning that ovulation will shortly occur and therefore armed with this information, the user is alerted to the fact that the LH surge/peak or other indicator will shortly occur and this is therefore less likely to be missed. Furthermore, if a high LH concentration or other indicator is detected in the absence of the positive indication or pre-warning by the other analyte, this can be assumed to be clinically insignificant and can be disregarded. A particularly useful analyte for this purpose is estradiol or a metabolite thereof, especially estrone-3-glucuronide (E3G). By existing technology, it is possible to measure both E3G and LH in a single body fluid sample such as urine using a single assay device. An appropriate test device is described, for example, in EP-A-703454.

The invention provides a method for determining the time of maximum fertility in the mammalian ovulation cycle, wherein testing is conducted over a period of days in the current ovulation cycle on samples of body fluid to detect a change in the concentration of analyte indicative of actual the event of ovulation, and wherein testing is conducted over a period of days in the current ovulation cycle on samples of body fluid to detect a change in the concentration of an analyte indicative of the imminent event of ovulation.

The invention provides as one embodiment a monitoring device for use in conjunction with one or more body fluid testing devices to provide an indication of the time of maximum fertility in the mammalian ovulation cycle, wherein:

a) said one or more testing devices provide test signals readable by said monitoring device, including a signal proportional to the concentration of a first analyte in a body fluid, which first analyte exhibits a detectable concentration change at about the time of ovulation in the cycle, and a signal proportional to the concentration of a second analyte in a sample of body fluid, which second analyte exhibits a detectable concentration change after the commencement of the cycle but before the concentration change of said first analyte becomes detectable; and b) in response to test signals provided by said one or more testing devices used in a series of tests conducted following the commencement of the cycle, said monitoring device provides an indication that fertility is elevated when said concentration change of said second analyte has been detected, and an indication that the fertility is maximum when said concentration change of said first analyte has been detected.

Preferably said first analyte is luteinising hormone (LH).

Preferably said second analyte is estradiol or a metabolite thereof.

A particularly suitable body fluid is urine.

Preferably no indication of maximum fertility is provided unless said concentration change of said second analyte has already been detected in the current cycle or is detected no later than the time at which said concentration change of said first analyte is detected.

Typically, the monitoring device comprises receiving means to receive a testing device, reading means associated with said receiving means to read said test signals, electronic processing means to interpret said test signals, and display means to provide said indications of fertility. In a preferred embodiment, said display means includes a visual indication in the form of a bar or similar symbol the height or length of which is altered in either a continuous or step-wise manner as the likelihood of conception increases, attaining a maximum height or length to indicate the most appropriate time in the cycle to attempt conception.

In another embodiment the inventor provides a monitoring device together with at least one body fluid testing device to provide said readable test signals.

The test kit can comprise a plurality of body fluid testing devices to provide said readable test signals. Preferably each of said testing devices provides a test signal proportional to said concentration of said first analyte and a test signal proportional to said concentration of said second analyte.

The invention provides as one embodiment a monitoring device for use in conjunction with one or more body fluid testing devices to provide an indication of the time of maximum fertility in the mammalian ovulation cycle, wherein:

a) said one or more testing devices provide test signals readable by said monitoring device, including a signal proportional to the concentration of a first analyte in a body fluid, which first analyte exhibits a detectable concentration change at about the time of ovulation in the cycle, and a signal proportional to the concentration of a second analyte in a sample of body fluid, which second analyte exhibits a detectable concentration change after the commencement of the cycle but before the concentration change of said first analyte becomes detectable; and b) in response to test signals provided by said one or more testing devices used in a series of tests conducted following the commencement of the cycle, said monitoring device provides an indication that fertility is elevated when said concentration change of said second analyte has been detected, and an indication that the fertility is maximum when said concentration change of said first analyte has been detected.

Preferably said first analyte is luteinising hormone (LH). Preferably said second analyte is estradiol or a metabolite thereof.

A particularly suitable body fluid is urine.

Preferably no indication of maximum fertility is provided unless said concentration change of said second analyte has already been detected in the current cycle or is detected no later than the time at which said concentration change of said first analyte is detected.

Typically, the monitoring device comprises receiving means to receive a testing device, reading means associated with said receiving means to read said test signals, electronic processing means to interpret said test signals, and display means to provide said indications of fertility. In a preferred embodiment, said display means includes a visual indication in the form of a bar or similar symbol the height or length of which is altered in either a continuous or step-wise manner as the likelihood of conception increases, attaining a maximum height or length to indicate the most appropriate time in the cycle to attempt conception.

In another embodiment the inventor provides a monitoring device together with at least one body fluid testing device to provide said readable test signals.

The test kit can comprise a plurality of body fluid testing devices to provide said readable test signals. Preferably each of said testing devices provides a test signal proportional to said concentration of said first analyte and a test signal proportional to said concentration of said second analyte.

In a more specific embodiment, the invention provides a method for determining the time of maximum fertility in the human ovulation cycle, wherein testing is conducted over a period of days in the current ovulation cycle on samples of body fluid obtained from an individual human subject to detect an elevated concentration of luteinising hormone (LH) indicative of the event of ovulation, wherein additionally testing is conducted over a period of days in the current ovulation cycle on samples of body fluid obtained from the individual human subject to detect an elevated concentration of estradiol or a metabolite thereof indicative of the imminent event of ovulation.

Preferably, therefore, testing is conducted over a period of days in the current ovulation cycle on samples of body fluid obtained from the individual human subject to detect an elevated concentration of estradiol or a metabolite thereof indicative of the imminent event of ovulation. In this embodiment of the invention it is convenient and advantageous if the estradiol or metabolite thereof are detected in the same body fluid samples as are used in the LH tests. Conveniently a single test is used to determine both LH and the estradiol/metabolite in a single body fluid sample.

Preferably an elevated LH concentration apparently indicative of the event of ovulation is disregarded unless an elevated concentration of estradiol or a metabolite thereof has been detected in the current cycle.

An important embodiment of the invention is a test kit comprising:

a) at least one body fluid testing device that provides a readable signal proportional to the LH concentration in a sample of the body fluid;

b) at least one body fluid testing device that provides a readable signal proportional to the estradiol/metabolite concentration in a sample of the body fluid;

c) an electronic monitor having reading means to read the readable signals and incorporating computer means to interpret the readable signals and to determine therefrom in conjunction with data from previous body fluid tests whether the event of ovulation in the current cycle is about to occur or has just occurred.

Preferably the test kit comprises a plurality of testing devices each of which provides a readable signal proportional to the LH concentration and a readable signal proportional to the estradiol/metabolite concentration in a single sample of the body fluid.

In this context a significant amount, in relation to the analyte concentration or concentration related test signal, will be dependent on the way in which the assay is formulated and the signal reading system adopted. An objective is to eliminate as far as possible misleading information arising from minor daily fluctuations in the LH concentration which are not indicative of the major rise in this concentration associated with the event of ovulation. In general, variations from the threshold of less than about 10%, and preferably less than about 15% should be ignored. Desirably the test format and reading systems chosen in a test kit for use in the invention should provide a test signal range which is sufficiently extensive to enable a ready distinction to be made between signals associated with such insignificant fluctuations and larger changes that are clearly of clinical significance. In particular we have found that where the testing system uses optical transmission through a porous test strip in which the signal is generated by specific binding of a particle-labelled reagent in a detection zone, an optical transmission change of at least about 15% can be regarded as potentially significant in relation to the related concentration of LH in a urine sample being tested.

In essence, in a method according to the invention, a high concentration of LH is not identified as being indicative of ovulation unless an adequately elevated level of estradiol or its metabolite has already been identified in the cycle or is identified at the same time as the elevated LH level.

To facilitate this it is necessary to determine what constitutes an adequately elevated level of the estradiol or its metabolite. This can be achieved in more than one way. One option is to establish either from population studies or from previous tests in the same individual subject a threshold level for the analyte around the time of ovulation. This can define a minimum level or intensity of a test signal associated with the estradiol/metabolite, and an algorithm rule can be established that the signal observed must reach this threshold before being regarded as adequately elevated. Alternatively, or in addition, a base line for the analyte can be established early in the cycle and/or from information from previous cycles in the same individual and the ratio of the current signal to the base line signal used as an indication of adequately elevated analyte concentration. The appropriate relationship between these signals can be established from previous experience with the individual under test.

Taking estrone-3-glucuronide (E3G) as an example of a suitable analyte for this purpose, the ratio of the test signal to the base line signal should preferably be less than about 0.7 and more preferably less than about 0.65. This assumes that the E3G is detected by a competition-format reaction and the intensity of the signal declines with increasing E3G concentration.

Because the fundamental objective of the present invention is to assist conception, the requirements placed on a testing method are different from those applicable to previous proposals which have centred on the objective of avoiding conception. We believe that in order to assist conception effectively, the user needs to be given from one to five days warning of the event of ovulation. Where the event of ovulation is defined by detecting the LH surge, the user should be given one to five days warning of this phenomenon. In the preferred embodiments of the invention this warning is provided by monitoring E3G. The period of advance warning can be regarded as one of "high fertility". This precedes the time of "peak fertility" associated with actual ovulation. It is therefore envisaged that in the human ovulation cycle the total interval encompassing the high and peak fertility states will be substantially shorter than the "safe period" that would be required in a monitoring system where the objective is to avoid conception. The need of the present invention dictate that the rise in the concentration of E3G used as a trigger to initiate the high fertility phase is greater than would be required to initiate a safe period for the purposes of contraception.

For the present purposes a convenient way of establishing a baseline for E3G in the human ovulation cycle is to measure the E3G concentration, for example, in urine at or about day 6 of a cycle. If desired, this baseline can be reset in every subsequent cycle by relying on further testing at this early time. However, we have found that once a baseline has been set for a specific user, it is generally unnecessary to repeat this aspect every cycle. Thus in subsequent cycles each E3G measurement can be related back to the previously established baseline to determine whether a significant rise in E3G concentration necessary to trigger the high fertility status has been achieved in the current cycle.

Where the measurement of LH is used to pinpoint ovulation this can also be related back to a baseline concentration. However, we prefer, for LH, to use a procedure of continuous testing (during the appropriate testing interval in each cycle) in which the changes in LH concentration are calculated on a progressive basis, for example, using a CUSUM style calculation.

If, as set out above, the testing regime does not require the establishment of an E3G baseline in each successive cycle, it may be unnecessary for testing to commence as early as about day 6 in the successive cycles. The testing commencement day can be related back to a day at a set interval in advance of the typical numerical day on which the event of ovulation (e.g. LH surge) has been recorded in one or more previous cycles.

Again using by way of example the measurement of E3G and LH in the human ovulation cycle, we can say that in a typical individual the baseline level for E3G is likely to be in the range of about 5 to about 15 ng/ml urine. Depending on the actual baseline signal for the particular individual the trigger for entering the high fertility status phase may occur at an E3G concentration of about 20 to about 40 ng/ml urine. Typically the ratio between the baseline concentration and the trigger concentration should be at least about 2.5 and preferably at least about 3.

For LH a trigger point to identify peak fertility is likely to lie in the range of about 35 to about 45 mIU/ml urine.

A preferred rule for allocating the testing commencement day in a cycle is that this should be a set number of days in advance of the mean numerical day in one or more previous cycles on which the LH surge/max was detected. Preferably this is at least 6, but preferably not more than 9 days, in advance of the mean LH surge day, more preferably about 7 days in advance. Preferably up to about 6 previous cycles in the same individual are used to provide historical data of the LH surge/max day for these purposes. This can include cycles in which no LH surge had been identified. Optionally for such cycles a nominal LH surge/max day can be allocated if the cycle length is typically of a "normal" duration, i.e. about 23 to about 37 days.

For identifying the LH surge/max day in any given cycle, an LH signal indicative of this event can be ascertained from population studies or information derived from the individual previously. This can set a minimum signal level below which the LH surge/max is not indicated. An alternative or supplemental approach is to observe the progressive increase in LH concentration during the first half of the cycle and to detect a significant rise of LH concentration over a cumulative mean. A sudden increase in the detected LH concentration optionally coupled with a minimum signal level as just described can, together, be used to provide clear evidence of the ovulation event. By adopting a method of the invention in which LH and E3G are simultaneously detected using a series of tests in the cycle, it is envisaged that 10 or more tests will be required in each cycle. However, the testing regime can be flexible. It is envisaged that the method of the invention will provide at least one day and generally more than one day warning of the LH surge/max event. The likelihood of achieving conception can therefore be facilitated.

An optional refinement of the method of the invention is to continue testing through to the end of the cycle to determine whether conception may have occurred. A calendar built into the electronic memory of the monitoring device can establish when a normal cycle in the individual under test would be expected to end. If the next cycle is late, this may be an indication of pregnancy. Test devices detecting hCG can be used to confirm pregnancy.

Although we prefer to use LH as the indicator of the ovulation event, it is also possible to use other analytes, especially pregnane-3-glucuronide (P3G) as an indicator that ovulation has occurred. In general this should be used (if at all) merely to confirm the indication already provided by an LH test result.

Within the generality of the invention a variety of strategies can be adopted in order to obtain maximum advantage from the LH concentration information and other data obtained.

The testing period during the cycle can be relatively restricted. For example, this can be over a period of days commencing from the earliest numerical day in one or more previous cycles on which the LH surge or peak has been detected, or from an average LH surge day. Alternatively it can be from a defined routine day e.g. day 6 in each cycle. However, continuous testing from the start of each cycle and indeed throughout all cycles can be conducted if desired. During the chosen testing interval tests should be conducted at least once every 48 hours, but usually not more frequently than once in 12 hours. A daily test is usually most convenient. This can be conducted at the same time each day in order to develop a routine that is convenient to the user.

Testing strategies for determining accurately a significant rise in the urinary concentration of E3G are described, for example in EP-A-706346. For example, an E3G concentration threshold can be established early in the cycle such as by means of a test on or about day 6 of the cycle and subsequent daily E3G testing can be compared with this threshold level to ascertain whether a significant rise in the E3G concentration is occurring and therefore the LH concentration can be expected to rise within the next few days. Alternatively a rise in E3G concentration can be calculated using CUSUM techniques.

As a desirable optional feature, the electronic monitor includes interface means to communicate with electronic data transmission means, such as a smart card or floppy disk. The data transmission means is used to transfer information to a computer means, such as a PC. This can be in the home to assist the user in understanding what the monitor is recording. More usually, such an electronic data transmissions means can be used to convey information from the home-use situation to a health professional, for example in a family planning clinic. The patient information stored in the electronic monitor can be processed by computer means, such as a PC in the clinic, to provide the health professional with a record of the patient's recent ovulation cycles. This can facilitate the provision of appropriate medical advice or treatment. It can also be used to change or supplement the algorithm or data store in the monitor.

The smart card interacts with the electronic monitor. In the context of the invention, the expression "smart card" is being used to mean, as a minimum, a semi-conductor memory device. These cards are available commercially as blanks from several manufacturers. By way of example, many have a standard physical format referred to as an "ISO format". A typical card will contain a non-volatile memory, i.e. the card does not need to contain a power source. The card therefore has a simple memory and generally needs to be coded to operate in a chosen manner. The procedures necessary for coding such cards are now routine. Coding enables the monitor to recognise the function or purpose of the card. For the purposes of the invention the memory capacity can be quite small, for example just a few hundred bytes, but blank cards are available with capacities of many megabytes and these can be used if desired. Again just by way of example, a card having a 512 byte non-volatile memory accessed by a I2C protocol is very suitable. Generally, as supplied by the manufacturer, a typical card is most useful as a simple data card. To alter the function the card should be initialised. Appropriate coding procedures are routine and in no way critical to the invention.

Within the context of the present invention such a card can be used for several different purposes.

In a first embodiment the card can act as a means for transferring stored data from the electronic monitor to another facility such as a computer (PC)in the office of a health professional. Upon insertion of the card into the receiving slot or other interface means of the monitor the card can record internally stored data in the memory of the monitor. Optionally the card can also transfer data into the monitor. The data that has been transferred to the card can be retained by the user for backup purposes, or used by a health professional.

In a further embodiment the card is used to record one or more events in the cycle. The card is interfaced with the monitor by the user to log the event on the same time base as the monitor-stored analyte test information. The card will log the monitor clock or calendar value each time it is interfaced with the monitor. Data held on the event card can be analysed by appropriate computer software and, if necessary correlated with test information retrieved from the monitor memory by a data card as set forth above. Typical events for which a designated card would normally be required include the timing of acts of intercourse, patient symptoms or the timing of therapy administration.

In another embodiment, a card is used as a static measurement card, associated with an additional different test that does not form part of the normal testing regime for which the monitor is set up. The static measurement card is interfaced with the monitor, the associated special test is performed (generally using a distinct testing device) and the test result recorded on the card. Optionally the test result can appear on the visual display of the monitor, but usually without affecting the normal monitor function. Examples of additional tests useful in the context of the invention are tests for the presence of or concentration of one or more other analytes in the body fluid. Typical analytes are human chorionic gonadotropin (hCG) associated with pregnancy, pregnanediol-3-glucuronide (P3G) and follicle stimulating hormone (FSH).

An important aspect of the invention is therefore a method of patient management in which the patient or other user (normally in the home) tests and records ovulation cycle information as described earlier in this specification using a monitor and one or more testing devices and downloads data (either stored memory and/or event timing and/or static test data) onto one or more data transmission means which are used to relay and input the stored information to computer means (such as a PC) operated by a health professional. The health professional advises the patient on the basis of the transferred information. Typically the advice can either be on the timing of intercourse to achieve maximum chance of conception, or the prescription of therapy and/or lifestyle change to enhance the chances of conception or to alleviate or regulate health problems or conditions that are revealed by the transferred data.

The type of computer software necessary to support any of the foregoing embodiments of the invention, involving data transfer to a PC or the like, is in itself neither complex nor unusual. The PC should incorporate, or be connected to, means for reading the electronic data transmission device. Such reading means are available commercially. This is facilitated by the use of a standard format data transmission means, such as a smart card as referred to above. Within the PC the software must be compatible with the form of the electronic information being transferred. The basic requirement is that the PC should provide the health professional or other user with a visual display conveying information about the status of the patient. Within the context of the invention this visual display can include a representation of one or more ovulation cycles (optionally including the current cycle), for example in graphical or calendar layout. The transmitted data should be incorporated into the chosen layout and thereby enable the health professional or other user to see at a glance the fertility status or one or more other characteristics of the specific individual. Where appropriate this can be combined with other stored health records associated with the individual.

By way of example only, a specific embodiment of a monitor and test device useful in the practice of the invention will now be described in detail with reference to FIGS. 1 to 12 of the accompanying drawings. These drawings are for the purpose of general illustration only, and are not to scale. The reader of this specification should also take note of the technical content of WO 95/13531 which provides examples of the manner in which the test device can generate a readable assay signal and a mechanism by which the reading device reads and interprets this signal and provides information to the user. An optimised test device/reader combination is described in detail also in EP-A-833145.

BRIEF DESCRIPTION OF THE DRAWINGS

FIG. 1a represents a general view of the upper surface of an electronic monitor or reading device of the invention, as seen from the front, showing the main user-related features of the device.

FIG. 1b represents a general view of the upper surface of the same device, but viewed from the rear.

FIG. 5 is a partial elevation looking into and along the slot from the right hand end.

FIG. 6 is a general view of an assay device as held by the user in an orientation appropriate for insertion into the reading device.

FIG. 7 is a general view of the opposite side of the assay device.

DETAILED DESCRIPTION OF THE DRAWINGS

Figure 2:
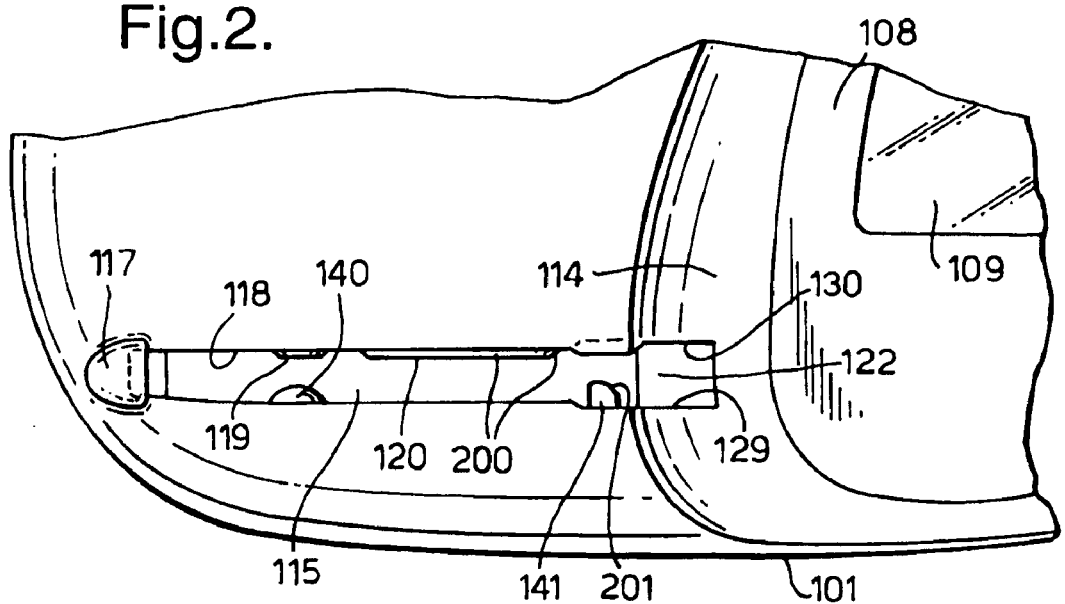
FIG. 2 represents a plan view of part of the device seen in FIGS. 1a and 1b, showing in detail a slot for receiving an assay device.

Referring to FIG. 1a, the reading device comprises a generally flattened oval body 100. The overall shape and proportions of the body are mainly aesthetic, and have no bearing on the present invention. Optionally the device can be provided with a lid (not shown). As depicted, body 100 has a front edge 101, a rear edge 102, and left-hand and right-hand edges 103 and 104 respectively. The upper surface 105 of body 100 is divided into a left-hand elevated region 106 of gently curving front-to-back cross-section and a right-hand portion 107 comprising a flat surface or plane 108 of lower elevation than left-hand portion 107. Towards rear edge 102 in surface 108 are some operating features important to the user. These include a display panel 109, shown as being of rounded rectangular shape although this is not critical. A push button 110 is mounted adjacent the right-hand edge 104. Button 110 can provide means by which the user can signal to the device that an ovulation cycle has commenced, usually the start of menstruation. The overall shape of body 100 can optionally include one or more indentations or cusps, represented by features 111 and 112, to provide the device with an aesthetic appearance or to render it more ergonomically attractive as a hand-held device. It is envisaged that the device can be held in the left hand of the user, and to facilitate this it can be provided with an optional depression, represented by feature 113, in the upper left-hand region 106 to act as a thumb grip. These aesthetic features are in no way critical to the invention. At the left of surface 108 is a sloping face 114 linking surface 108 with elevated region 106. From the centre of face 114 a receiving slot 115 extends horizontally towards the left-hand edge 103 of the device. Slot 115 extends almost as far as left-hand edge 103, and terminates beneath a small canopy 117 moulded into the elevated portion 106 of the device. In FIG. 1a the rear wall 118 of slot 115 can be seen, and features a switch actuating mechanism 119 to initiate reading of an assay device (not shown) when inserted into the slot, and also a rectangular cover 120 of a reading system (hidden within the body of the reading device) to obtain information from an inserted assay device. Switch 119 is described below in greater detail with reference to FIGS. 3, 9 and 10. Surface 108 extends into the slot. Other features of the slot visible in FIG. 1a are that it is substantially parallel-sided throughout most of its length, but a region 126 of the nearer face tapers inwardly slightly as it approaches the canopy. At the other, open, end 122 of the slot there is a forwardly extending lip 127 at the top edge 128 of the rear wall 118. The slot is widest at its open end 122, because both the front wall and the rear wall are stepped outwardly in regions 129 and 130 respectively.

Referring to FIG. 1b, in the forward wall 126 of slot 115 are two projecting spring-loaded buttons 140 and 141, one (140) being directly opposite the actuating switch 119 and the other (141) being near the mouth 122 of the slot, opposite the lip 127 that extends from the rear wall 118. Situated horizontally between the two buttons is a rectangular recess 142 behind which is an illuminating system (not seen) which forms part of the assay reading mechanism. Recess 142 is situated directly opposite the protruding cover 120 of the reading system in the opposite wall of the slot. As seen in this rear view, the device also includes a push button 143 located in edge 103 of the device that can be actuated easily by the user's left hand when holding the device. Button 143 is an on-off switch for the device. Edge 102 of the device adjacent elevated region 106 includes a horizontal slot 144 to receive a smart card or the like (not shown).

Referring to FIG. 2, the features of slot 115 can be seen more clearly. Additional features visible in FIG. 2 are that the rectangular cover 120 for the reading system extends outwardly from the rear wall 118 of slot 115 and has sharply bevelled edges 200. Button 141 has a bevelled face 201 adjacent the mouth of the slot.

Figure 3:
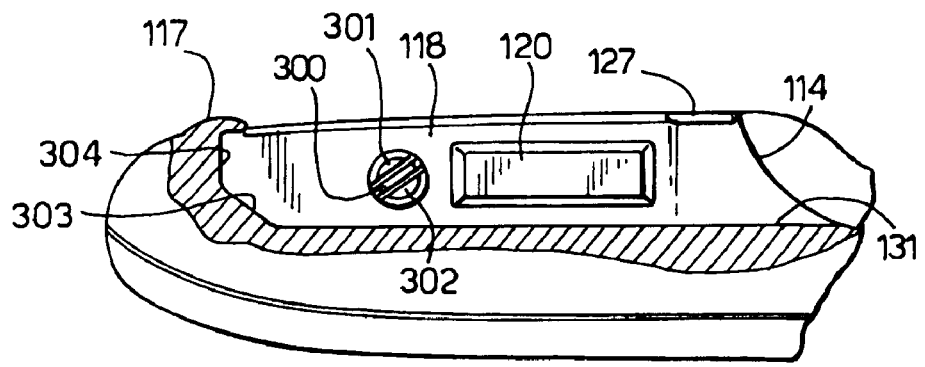
FIG. 3 is a partial cross-section of the reading device, taken on the longitudinal axis of the slot, showing the rear wall of the slot.

FIG. 3 shows the rear wall 118 of slot 115. The switch actuator 119 is divided into three components. The overall form is circular, but it comprises a diagonal central portion 300 extending across the entire width of the actuator, and two arcuate portions, 301 and 302, one on each side of the diagonal. The arcuate portions are fixed, but the central diagonal portion is depressible inwardly to actuate reading by the device. FIG. 3 also shows that a region 303 of the flat floor 131 of the slot, adjacent canopy 117, slopes upward sharply to meet the end wall 304 of the slot beneath the canopy.

Figure 4:
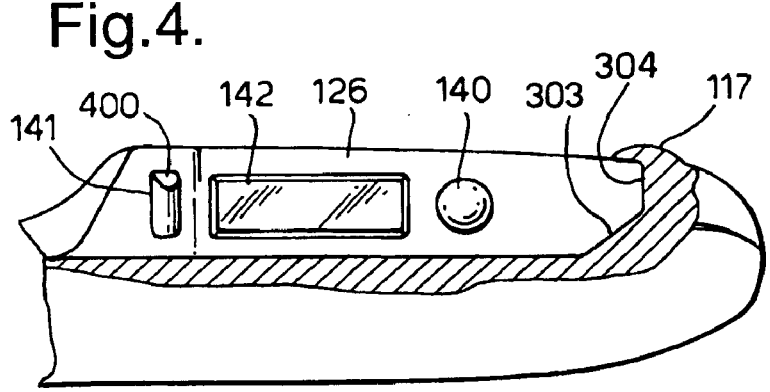
FIG. 4 is a partial cross-section of the reading device, again taken on the longitudinal axis of the slot but viewed in the reverse direction, showing the opposite wall of the slot.

FIG. 4 shows the opposite wall 126 of slot 115, including the two spring-loaded buttons 140 and 141. Button 141 adjacent the mouth 122 of the slot is of asymmetric shape and its top 400 is bevelled downwardly. The upwardly sloping region 303 of floor 131 of the slot can be seen beneath canopy 117.

The view along slot 115 as seen in FIG. 5 shows that the underside 500 of projecting lip has a convex curved surface. Other features seen in FIG. 5 are the bevelled pressure button 141, the protruding reading system cover 120, the canopy 117 at the far end of the slot, and the upwardly sloping floor 303 beneath the canopy.

FIG. 6 shows an assay device comprising an elongate body 600 and a removable cap 601. The left hand portion 602 (as seen in FIG. 6) of body 600 is of narrower cross-section than the main portion 603 and tapers sharply at its extreme left hand end 604. This tapering results from:

a) Front face 605 of the device being bevelled towards the left hand end; and b) Lower surface 606 being angled sharply upwards at the left hand end.

There is a long rectangular window 607 in the front face 605 of the narrower portion 602 of the body, having angled sides 608 extending into the body moulding. This window reveals an assay strip 609 within the device and, as shown, this includes two assay result zones 610 and 611.

Referring to FIG. 7, which shows the opposite side of the assay device, the opposing face 700 of the narrower portion 602 of the body also incorporates a rectangular window 701 recessed into the body. This window reveals also the strip 609 and the same detection zones 610 and 611, as seen through the other window. In this same face of the device, between window 701 and the extreme tip 702 are a pair of arcuate recesses 703 and 704 separated by a diagonal portion 705 which is flush with the remainder of the device surface at this point.

Figure 8:
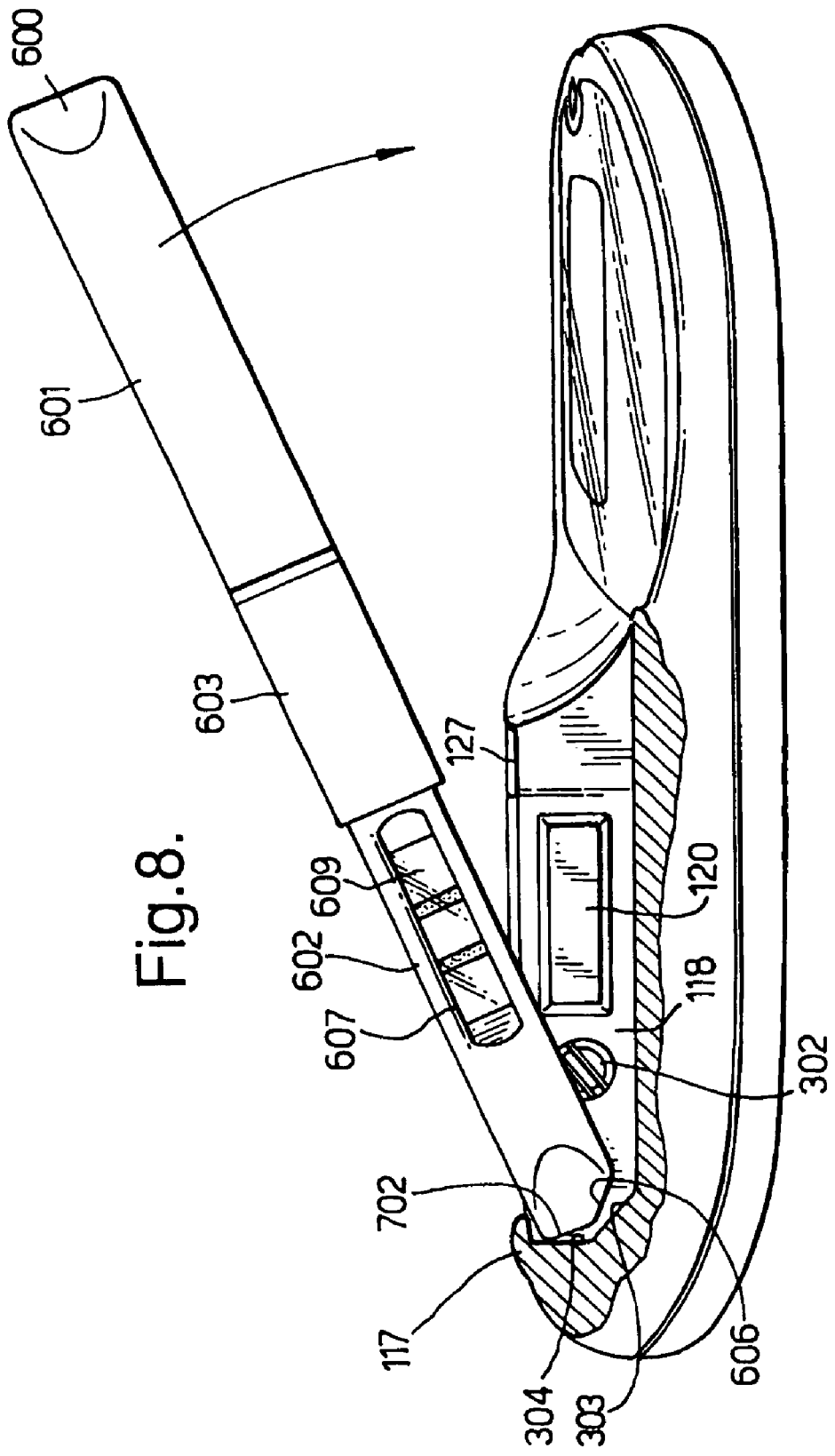
FIG. 8 is a partial cross-sectional elevation of the reading device and assay device during insertion, viewed from the front of the reading device.

FIG. 8 shows the assay device 600 being inserted into the reading device. The tip 702 of the assay device body has been placed beneath canopy 117 and, at about the mid-point of the narrower portion 602 of the body, it is contacting and resting the upper part of pressure button 140, although this is not seen in this drawing. This is a stable position, and it requires finger pressure by the user downwardly on the body 603 and/or cap 601 of the device to push the device into a more horizontal orientation within the slot, against the resistance created by pressure button 141 which would be displaced by such motion. This drawing also shows, in broken lines, the position that the assay device needs to occupy when correctly inserted in the reading device for accurate reading. This correct position requires the assay device to be fully horizontal (relative to the reading device floor) with tip 702 fully home under canopy 117. It can also be seen that the upwardly sloping portion 606 of the tip 702 of the assay device matches the upward slope 303 of the floor of the slot beneath the canopy. When the assay device is correctly inserted in the slot, the broader portion 603 of the body is retained snugly beneath the projecting lip 127 of the rear wall 118 of the slot.

Figure 9:
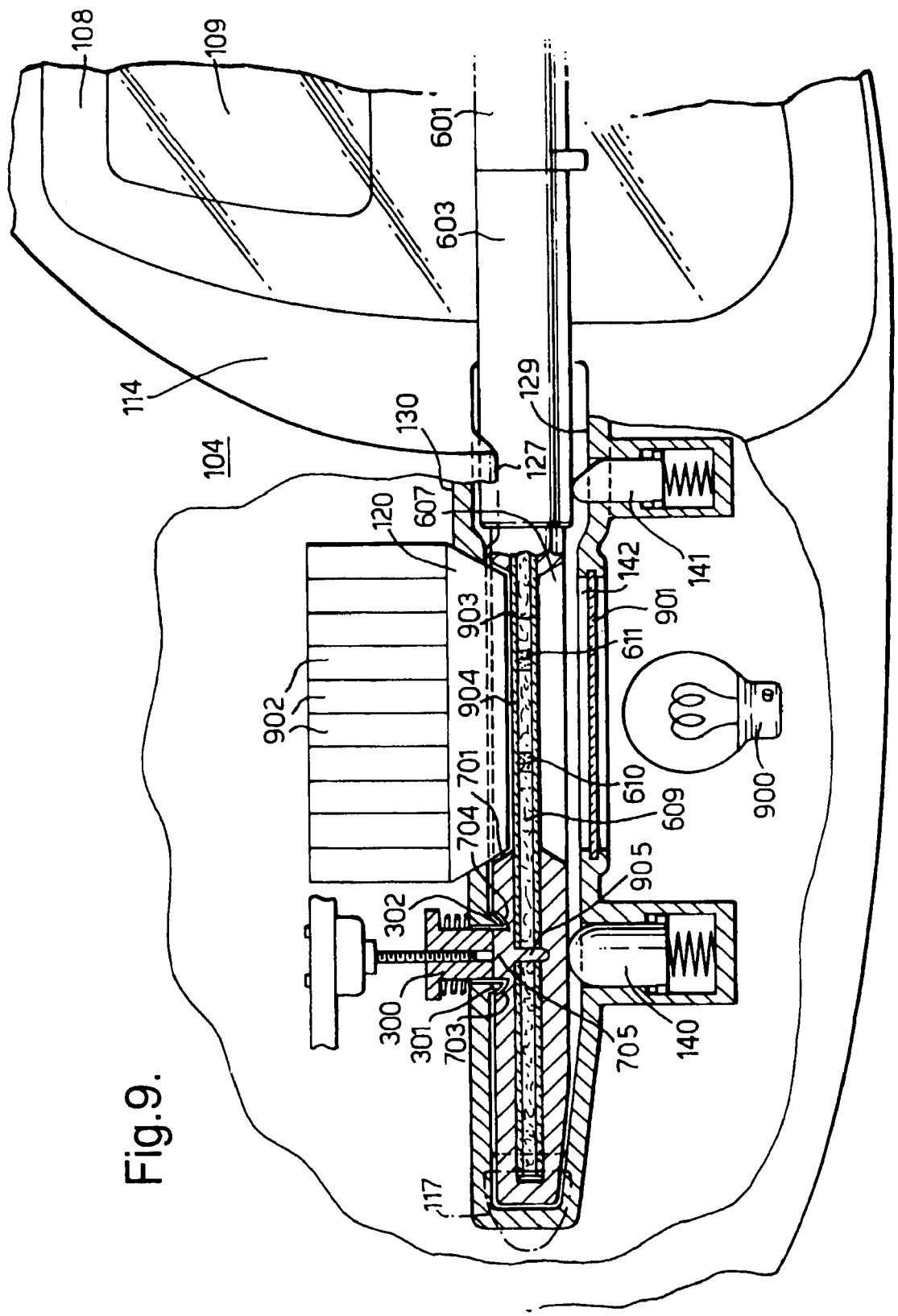
FIG. 9 is a plan view, partially cross-sectional and partially cut away, of the slot with the assay device correctly inserted therein.

Referring to FIG. 9, the correctly inserted assay device is locked in place by a combination of features. It is urged against the rear wall 118 of the slot by pressure from the two pressure buttons 140 and 141. The protruding cover 120 of the reading system fits precisely into the window recess 701 in the assay device body. The fixed arcuate portions 301 and 302 of switch actuator fit precisely into the arcuate recesses 703 and 704 in the assay device body, and the central diagonal portion 300 of the switch is depressed by the diagonal body portion 705 between the two recesses. Depression of the portion 300 of the switch actuator causes reading of the assay device by a mechanism described below with reference to FIG. 10. The objective is to provide a unique three-dimensional situation in which the switch actuator is actuated by the received assay device. The positions of the canopy 117 and the protruding lip 127 are shown in broken lines. The broader portion 603 of the body of the assay device is accommodated within the outwardly flared mouth of the slot.

Other features shown in FIG. 9 are an illumination system 900 behind an optical diffuser 901 in the forward wall 126 of the slot, and a series of optical sensors 902 behind the cover 120 on the rear wall 118 of the slot.

These features are simply represented diagrammatically as they are not critical to the present invention. Appropriate examples of such features are described in WO 95/13531.

Features seen within the partial cross-section of the assay device are the assay strip 609 sandwiched on each side by a transparent plastics sheet 903 and 904, the two detection zones 610 and 611 in the strip, and a pin 905 in the assay device moulding which extends through the assay strip and covering sheets to provide during manufacture of the device a precise location means for the two detection zones. Examples of these features are also fully described in WO 95/13531.

Figure 10:
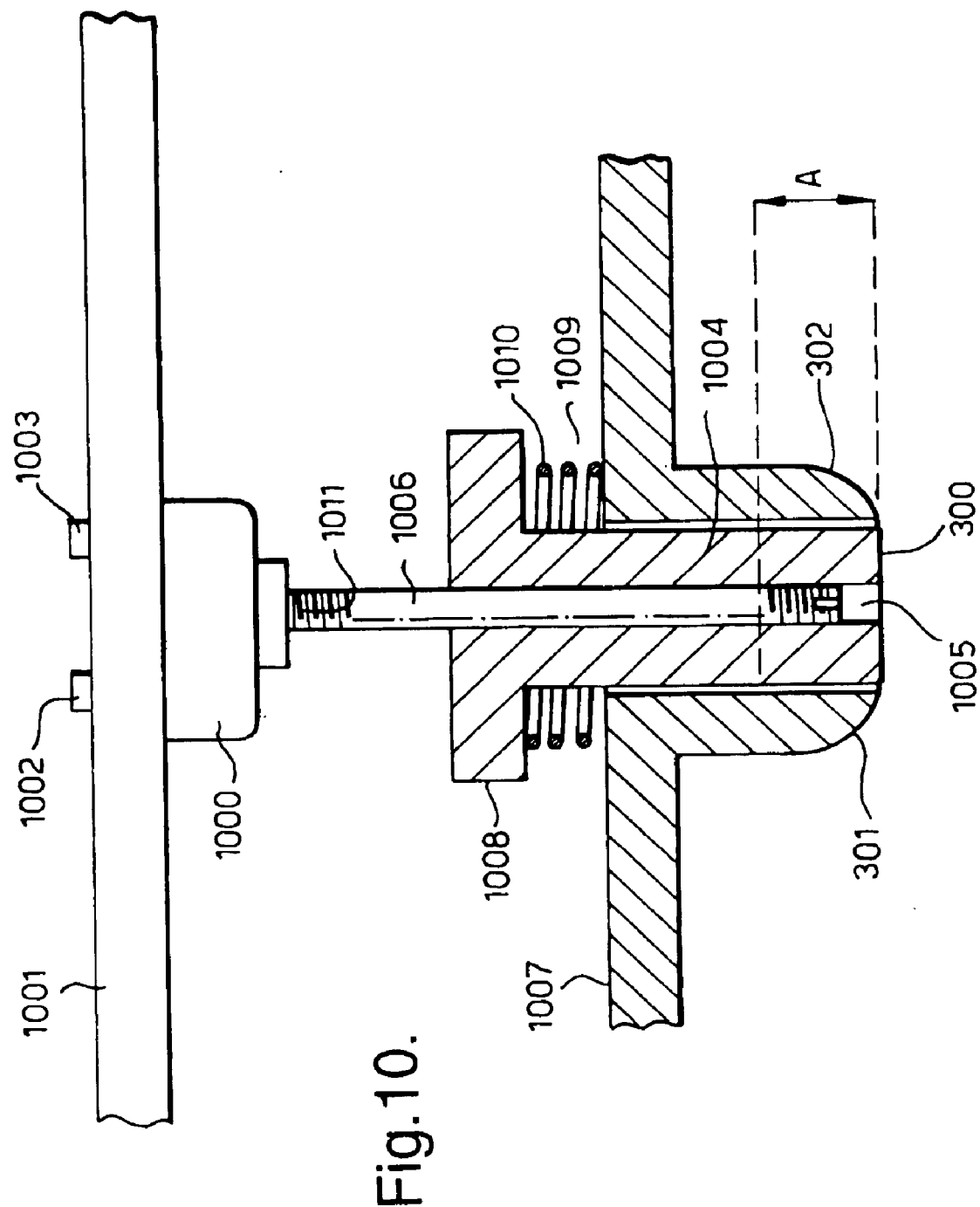
FIG. 10 is an enlarged plan view, in partial cross-section, of the switch actuating mechanism of the reading device.

FIG. 10 shows the switch actuating mechanism of the reading device in greater detail. The actual switch 1000 which is connected to the electronic processor within the reading device is itself within the interior of device, body 100 and in the preceding drawings is only visible in the partly cut-away FIG. 9. The actual unit 119 which is visible on the rear face of slot is a separate mechanical construction which makes contact with and operates switch 1000 during use. As depicted in FIG. 10, switch 1000 is situated on a printed circuit board 1001. At the rear of circuit board 1001 are two switch contacts 1002 and 1003.

The mechanical construction which interacts with a correctly inserted testing device is located in the rear wall of slot. As already described, the mechanism comprises two outer fixed portions 301 and 302, and a central movable portion 300 which is displaced inwardly when the testing device is correctly inserted. As depicted in FIG. 10, the movable portion 300 of the actuating mechanism comprises a hollow shaft 1004 which rests between the two fixed portions of the mechanism, and forms a freely-sliding bearing between 301 and 302. A threaded passageway 1005 extends axially through the entire shaft and engages with a long threaded screw 1006 held within the shaft. The shaft extends beyond the inner face 1007 of the slot wall and terminates in a flange 1008. The width of flanged portion of the shaft exceeds the width of the channel between the two fixed portions of the mechanism which accommodate the bulk of the spine. A gap 1009 exists between the flange and the wall of the slot, and within this gap is a helical spring 1010, the ends of which abut the flange and the inner wall surface. Spring 1010 acts to lightly bias the position of the shaft so that the end 1011 of the screw abuts the switch when the mechanism is in its rest position, which is as shown in FIG. 10. The force of spring 1010 is less than the force required to actuate the switch. Threaded screw 1006 extends beyond flange 1008. During manufacture of the reading device, screw 1006 can be adjusted so that the outer surface of central shaft 300 is at a distance A displaced from the tips of fixed portions 301 and 302 when contact is established within the switch. Control of this manufacturing adjustment can be achieved by sensing the switch contacts.

During the recommended mode of insertion of the assay device into the reading device, as generally illustrated in FIG. 8, the "toe" of the assay device is placed beneath the canopy 117 and finger pressure forces the assay device downwardly, pivoting against the fulcrum created by the lip of the canopy, and "snapped" past the various features which protrude from either wall into the void of the slot. The protruding cover 120, and to a lesser extent the fixed portions of the actuating switch and protruding lip 127, act as cams which force the body of the device away from the rear wall and against the two pressure buttons. As the assay device is rotated downwardly and the protruding cover and fixed portions of the actuating switch begin to engage with their appropriate recesses in the assay device body, the pressure created by the pressure buttons forces the assay device towards the rear wall of the slot and it can "snap" into position beneath the protruding lip. The curvature of the underside of the protruding lip facilitates this final motion of the assay device into its appropriate reading location. If the assay device is moulded from plastics material, such as polystyrene, as is conventional today in mass-produced diagnostic devices, it can have sufficient flexibility to distort and facilitate this motion. Indeed, the natural resilience of the assay device moulding can be exploited to advantage, because the deformation and subsequent release when the assay device is correctly received within the reading device can enhance the "snap" engagement between these two kit components. The edges of the assay device moulding, and of the points of contact on the reading device, can be radiused to facilitate sliding motion between these components, and to avoid situations in which the two components might jam together.

It is also possible for the user to insert the assay device into the slot to reach its correct reading position by placing the tip of the device in the open end of the slot and pushing the device horizontally until it is fully home in the slot. At the conclusion of this alternative procedure the assay device will again be held precisely in place by the various interactions described above.

If for any reason the assay device is incorrectly inserted into the slot during normal use, the precise registration of these various features will not be realised. The actuating switch will not be depressed. If desired, a supplementary sensing mechanism can be incorporated to detect the presence of an incorrectly inserted assay device so that a warning signal may be conveyed to the user that the assay device is not in its correct location.

The body of the reading device, including the walls and floor of the slot, can be moulded from durable plastics material, such as polystyrene. The pressure buttons, and the projecting portions of the switch-actuating mechanism are preferably made from more robust material, because these must withstand repeated contact with the disposable testing devices over an extended period of use. So-called "hard engineering plastic", such as ABS, is ideal. This has good dimensional stability and is harder than polystyrene. The material should have natural bearing properties. An ideal commercially available ABS is "Delrin".

The precise form and relationship of the various features described above, which provide a positive three-dimensional interlock when the assay device is correctly inserted, are for the purpose of example only. The skilled reader will readily appreciate that a wide variety of alternative profiles and constructions can be used to achieve a functionally comparable positive interlocking action.

Many assay devices are described in the technical literature with suggestions that the assay result can be read using optical equipment. The use of fluorescence emission, or light reflectance, is often suggested. Such techniques are mostly appropriate for use in sophisticated laboratories, although optical reflectance is used in commercially-available blood glucose tests. In WO 95/13531 we describe reading systems using optical transmission through an assay strip or similar membrane.

The assay device/reader combination can be supplied to the consumer as a single test kit. In general however, whereas the reader will be a relatively permanent unit which the consumer can use time and again (and which may be provided with an electronic memory/data-processing facility which enables the results of many sequential assays to be evaluated) the testing devices will be intended for use only once and thereafter will be discarded. Accordingly, the test devices may be supplied to the consumer separately from the reader, e.g. in multi-packs.

By ensuring precise interlocking between the testing device and the reader, and also ensuring precise registration of the location of the detection zone within the testing device itself, the testing zone will be presented to the reader in a constant pre-determined position every time a testing device is inserted into the reader. The construction of the optical system within the reader (light source and sensors) can therefore be kept as simple as possible, because it is not essential for the sensors to include any scanning facility, for example, which would otherwise be required if the exact location of the detection zone was not known. By avoiding the need for a sophisticated optical reading system, the cost of the reader/monitor may be reduced. Simplification of the optical reading system may also enable the reader/monitor to be of small size which will assist convenient and unobtrusive use in the home. Of course, a scanning facility can be included in the reader if desired.

An additional benefit of providing an internal registration system which ensures precise location of the detection zone within the test device, is that automated manufacture and quality control of the testing devices can be facilitated. Because it is envisaged, for example, in the case of an ovulation cycle monitor, that the consumer will need to use several testing devices each month, the testing devices may need to be manufactured in large numbers at low cost. Internal registration can facilitate automated manufacture and high throughput.

In principle, any electromagnetic radiation can be used to effect a transmission measurement. The electromagnetic radiation should preferably be capable of being rendered diffuse. Preferably the electromagnetic radiation is light in the visible or near-visible range. This includes infra-red light and ultra-violet light. It is generally envisaged that the detectable material used as a label in the assay is one which will interact with light in the visible or near visible range, e.g. by absorption. The wavelength of the electromagnetic radiation chosen is preferably at or near a wavelength which is strongly influenced, e.g. absorbed, by the label. For example, if the label is a substance which is strongly coloured, i.e. visible to the naked human eye when the material is concentrated, the ideal electromagnetic radiation is light of a complementary wavelength. Particulate direct labels, for example, metallic (e.g. gold) sols, non-metallic elemental (e.g. Selenium, carbon) sols, dye sols and coloured latex (polystyrene) particles are ideal examples. For instance, in the case of blue-dyed latex particles, the ideal electromagnetic radiation is visible red light which will be strongly absorbed by the blue particles.

A primary advantage of the use of diffuse light or other radiation in this context is that the reading of the assay result is much less likely to be adversely influenced by blemishes or contaminating material on the assay device. For example, dirt or scratches on the assay device in the region through which the radiation must be transmitted could strongly interfere with the accuracy of the determined result if focussed rather than diffuse light is used. By the use of a diffuse light source, it is possible to provide an assay result reader which can accurately interpret the result of an assay conducted even in an essentially transparent assay device without the assay result being adversely affected by minor contamination or damage (e.g. superficial scratches) to the assay device.

Desirably, the electromagnetic radiation from the source is pulsed. By synchronising the detectors (sensors) so that they function only in phase with the pulsed radiation source, it is possible to eliminate any background interference that might be caused by external radiation, e.g. ambient light. Home-use assays will mostly be conducted under circumstances of natural daylight or, even more often, artificial light. Artificial light is usually of a pulsed nature (typically 50–100 Hz) caused by the alternating nature of electricity supplies. By adopting a pulsed radiation source for the illumination of the assay device within the reader, the intrusion of natural daylight can be ignored. By selecting the pulse frequency such that it is sufficiently different from the prevailing artificial light, any interference due to artificial light can also be avoided. Preferably the pulse frequency of the energy should be at least about 1 kHz. An ideal pulse frequency is about 16 kHz. The electronics necessary to achieve synchronous pulsed sensing are familiar to those skilled in the art. The use of pulsed light is very advantageous because it renders it unnecessary for the monitor to be "light tight", thus simplifying its construction.

The source of light or other electromagnetic radiation can comprise entirely conventional components. Ideal examples are commercially available LED's, preferably chosen to give a suitable wavelength of light that is strongly absorbed by the detectable material concentrated in the test zone(s). Light from the LED's should be passed through a strong diffuser before reaching the assay device. If desired, an array of LED's which are energised in turn can be used.

Suitable diffusers can be made, for example, from plastics materials, and are available commercially. If necessary, the light-scattering properties of the diffusing material can be enhanced by including particulate materials such as Titanium dioxide and Barium sulphate. An ideal diffusing material comprises polyester or polycarbonate, containing Titanium dioxide. A good inclusion level for the particulate material is at least about 1% by weight, preferably about 2%. By the use of a diffuser, all relevant regions of an assay strip may be measured simultaneously, and differences in light output from the source are eliminated.

The sensor(s) to detect emergent light can be conventional components such as photodiodes, e.g. silicon photodiodes.

Preferably, a second diffuser, which can be made from the same material as the primary diffuser, is located in front of the sensor(s). This ensures that the view seen by the sensor is not affected by the presence or absence of a test strip in the reading head. In consequence, the monitor can be calibrated in the absence of a test strip, and then measure an assay result in the presence of an assay strip.

By employing a uniform light source it is possible to provide a reading system for test strips and the like which is relatively tolerant to variation in the placement of the test zone(s) from one strip to another, in the absence of a scanning sensor. However, very substantial benefits in terms of assay accuracy are obtained if test zone placement is controlled, as described herein.

As indicated earlier in this specification, for the purposes of enhancing the likelihood of conception, assay devices have already been marketed which enable the user to monitor the urinary concentration of luteinizing hormone (LH) which peaks sharply approximately one day in advance of ovulation. Daily testing of urinary LH concentration is conducted, for example using "dipstick" technology with the assay result being provided by a coloured end point, the intensity of the colour being proportional to LH concentration. By providing the consumer with a colour chart which enables the daily result to be compared against a standard, the "LH surge" can be detected simply by eye. Nevertheless a need still exists to extend the currently available qualitative home-use testing technology into the area of precise quantitative testing.

The improved test kits of the invention can be used in the determination of any body fluid analyte useful in the monitoring of the human ovulation cycle, for example by the determination of one or more hormones or metabolites thereof in body fluid, such as urine, for example either LH and/or estrone-3-glucuronide (E3G). The last few decades have seen much research conducted into ways of enhancing "natural" family planning, in which physiological parameters indicative of the status of the ovulation cycle are monitored. In EP-A-706346 we particularly describe such a method which uses the measurement of urinary estradiol or metabolites thereof, especially estrone-3-glucuronide (E3G), to provide a warning of the onset of the fertile phase. Related methods are described in EP-A-656118, EP-A-656119 and EPA-656120. Associated testing devices and test kits are described in these specifications, and also in WO 96/09553.

Within the context of the invention it is envisaged that a home-use sample liquid testing device will generally include a porous carrier material, such as a strip, through which applied sample liquid such as urine can permeate and wherein the assay result occurs by means of specific binding of a detectable material in a precisely-defined region (detection zone) of the carrier, such as a narrow line or small dot, containing an immobilised specific binding reagent. Localisation of a detectable material in such a detection zone can be determined accurately in a simple and cost-effective manner. Home-use devices for the analysis of urine, for example in pregnancy tests and ovulation prediction tests, are now widely available commercially. Many such devices are based on the principles of immunochromatography, and typically comprise a hollow casing constructed of plastics material containing a porous assay strip carrying pre-dosed reagents. The reagents within the device may include one or more reagents labelled with a direct label, such as a dye sol, a metallic (e.g. gold) sol, or a coloured latex (e.g. polystyrene) microparticle, which are visible to the eye when concentrated in a comparatively small test area of the strip. The user merely needs to apply a urine sample to one part of the casing to initiate the assay. The assay result becomes visible by eye within a few minutes without further action by the user. Examples of such devices are described in EP-A-291194 and EP-A-383619. Sample collection is conveniently achieved by means of a bibulous member which forms part of the device and which can readily take up sample liquid, e.g. from a urine stream. Optionally the bibulous member can protrude from the casing of the device to facilitate sample application. In addition to the specific examples of detectable materials already mentioned above, other materials can be used which block or reflect the electromagnetic radiation, rather than absorb it, e.g. "white" particles such as latex particles in their natural uncoloured state. Alternatively, the label can be a reactant or catalyst which participates in the generation of a radiation absorbing or radiation-blocking material, e.g. an enzyme which reacts with a substrate to produce a detectable material, such as a coloured material, in the detection zone.

It is generally envisaged that the material of the casing will be opaque, e.g. white or coloured plastics material, but the casing can be translucent or indeed transparent if desired.

The illuminator can consist of a series of LEDs embedded in or placed behind a diffusing medium which provides a uniform and diffuse illumination of the test strip covering the reference and signal zones.

The incorporation of a diffuser between the apertures and the test strip is beneficial for calibration purposes. In order to calibrate each of the optical channels in the absence of the test strip it is highly desirable that each detector is collecting light from the same areas of the illuminator as is the case when a test device is present. The diffuser can be selected to be the dominant diffuser in the optical path so that the introduction of the test strip does not contribute significantly to changes in the illumination distribution observed by the detectors. In addition, the diffuser element can enable the optical assembly to incorporate a 'wipe clean' surface, desirable for long-term repeated performance of the optical assembly. By modulating the intensity of the illuminator, the optical channels can be calibrated, without the aid of moveable parts, 'invisibly' to the user prior to the insertion of a test device.

The test strip can consist of an optically diffuse layer of nitrocellulose or the like, preferably sandwiched between two layers of optically clear film, e.g. of polyester such as "Mylar". The clear film protects the nitrocellulose within which the assay reactions take place. Making reflectance measurements through thin transparent films is particularly difficult because of problems arising from specula reflections. Transmission measurement allows the optics to be constructed orthogonal to the measuring surface and minimises the adverse effects of reflection. Ideal test strips can be made of nitrocellulose and similar diffuse membranes. Preferably they do not exceed about 1 mm thickness.

The constituent parts of the casing can be moulded from high impact or similar plastics materials such as polystyrene and polycarbonate and held together by "push fit" clips or threaded screws or any other appropriate mechanism.

It will be appreciated that the overall layout and general shape of the monitor can be subject to very considerable variation from that described above without departing from the scope of the invention. The general shape and layout of the reading head is dictated by the need to co-operate effectively with the assay device but this shape can be varied considerably. The layout and nature of the user accessible controls and information display features can likewise be subject to considerable variation and are dictated to a large extent by aesthetic considerations.

The detailed electronics of a monitoring device capable of assimilating, remembering and handling analyte concentration data, as well as providing the preferred electronic features of the device discussed herein, and where appropriate predicting future events, such as the fertility status in an ovulation cycle on the basis of such data, can readily be provided by those skilled in the electronics art once they have been advised of the factors that such a device must take into consideration, and the information that the device must provide for the user. The individual features can be entirely conventional, and those familiar with the art of electronics will appreciate that other combinations and arrangements of such features can be employed to achieve the objectives of the invention. For example, so-called hard-wired systems, and neural networks, can be used in place of conventional microprocessors based on "chip" technology.

Information can be conveyed to the user by means of a liquid crystal or LED display, for example. If desired, information on the state of fertility can be conveyed by a simple visual indication, e.g. a combination of colours showing, for example, green for infertile and red for fertile. Alternatively, or in addition, the display panel can provide a visual indication of the relative LH concentration or degree of fertility by means of a coloured or otherwise distinctive region such as a bar the length or height of which changes in either a continuous or step-wise manner. Thus, for example, a distinctively coloured bar can attain maximum height or length to indicate the most appropriate time to attempt conception. Simple visual information of this nature can be supplemented if desired by other visual or audible such as symbols or words appearing in the display panel.

Figure 11:
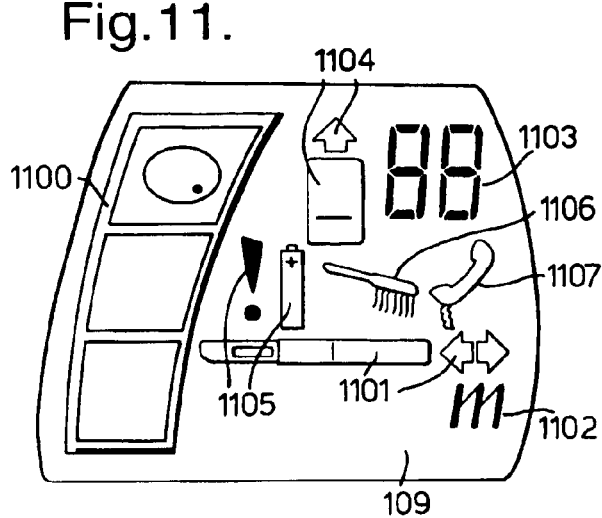
FIG. 11 shows a selection of visual symbols that may be displayed by the reading device.

FIG. 11, not to scale, shows a typical selection of symbols that can be used in such a visual display. In normal use, not all of the symbols would be revealed to the user at the same time. The type and arrangement of symbols shown in the display is not critical to the invention. However it is preferable that there should be some distinctive indication of the fertility status. Preferably this is by means of a symbol (1100) that varies in size, shape or content. Other instructions or indications that can usefully be provided to the user include:

Insertion or removal of a test device (1101).
A hint that a new ovulation cycle should be commencing (1102).
The numerical day of the cycle (1103).
Insertion of a smart card or the like (1104.
Battery flat (1105).
Clean the device (1106).
Seek "helpline" advice (1107).

Figure 12A:
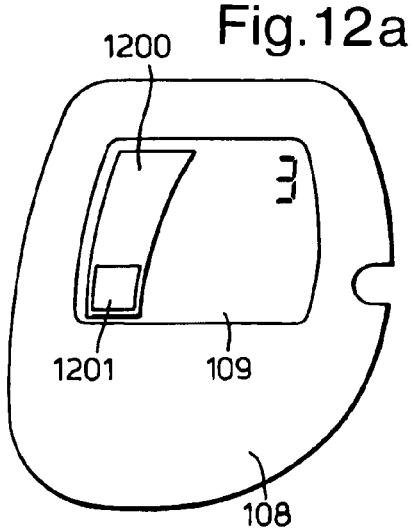
FIGS. 12a to 12c show stages in a variable display indicating relative fertility.
Figure 12B:
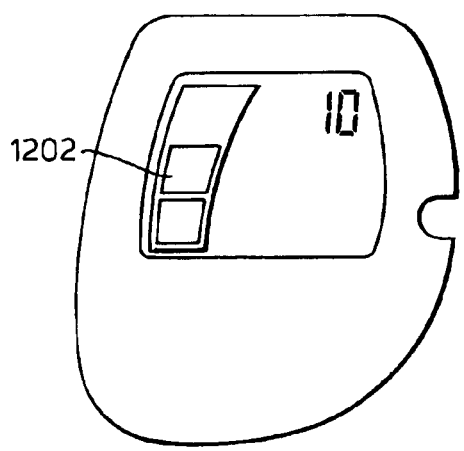
Figure 12C:
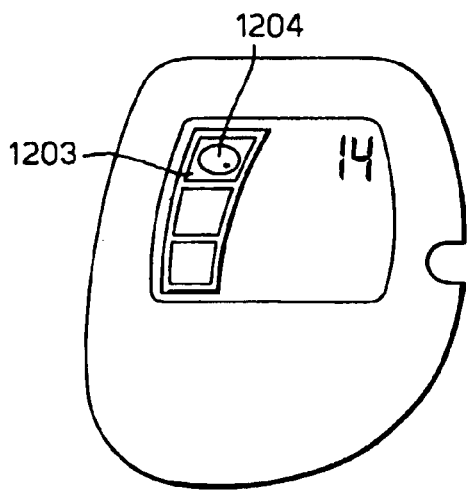

FIGS. 12*a* to 12*c* show a sequential display indicative of the ovulation status. The primary feature of the display is a delineated bar (1200) or other shape, the area within which is progressively filled to indicate fertility status. Thus as illustrated in these drawings, FIG. 12*a* shows a low fertility level indicated by only one third (1201) of the bar being filled. This may occur at a very early stage in the cycle, for example day 3. By day 10 of the cycle as the event of ovulation approaches, the fertility status can be higher, indicated by two thirds (1202) of the bar being filled. When the testing indicates that the event of ovulation has just occurred (or is immediately about to occur) the entire area of the bar can be filled. This represents peak fertility. The final portion (1203) of this area within the bar can optionally include an additional symbol, such as an "egg" (1204), to emphasise this status to the user. This visual display can be supplemented optionally with wording placed alongside the bar, e.g. "Low", "High" and "Peak".

Figure 13:
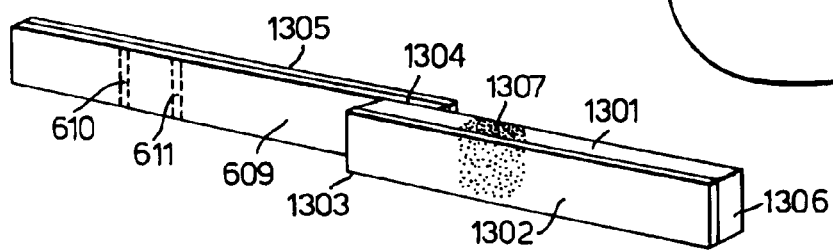
FIG. 13 represents a test strip forming part of the assay device seen in FIG. 6.

FIG. 13 is referred to in the following example.

EXAMPLE

The following example is a test kit according to the invention, useful in the identification of the event of ovulation.

The test kit comprises an electronic monitor, as described above with reference to the drawings, plus a number, e.g. 10, of identical disposable testing devices.

The exterior of each testing device is as depicted in FIGS. 6 and 7. The nitrocellulose test strip including the detection zones 610 and 611 is partially visible through the windows in the casing 602 of the test device. The remainder of the test strip and also a sample collector are hidden within the device casing and the cap 601. Essentially the complete test strip consisted of a sample collector made from non-woven polyester/viscose fabric backed with plastics material as described in EP-A-833160 containing two populations of latex particles as described below. This sample collector protrudes from the device when the cap 601 is removed. The sample collector feeds into a backed nitrocellulose strip containing the two detection zones visible from the exterior of the casing and which can be read by optical transmission as described above. For the purposes of the present invention, the constructional details of the test devices is not critical, provided that each test device can receive a urine sample and provide from that sample in the respective detection zones an optically readable signal proportional to the concentrations in that sample of E3G and LH. For the purposes of this example the readable signals are generated by binding of coloured latex particles in the two detection zones. The E3G related signal is the result of a "competition" reaction and accordingly the E3G related signal diminishes in intensity with increasing E3G concentration. The LH related signal is generated by means of a "sandwich" reaction and its intensity increases with increasing LH concentration.

If desired the signals generated by the device can be standardised against known concentrations of E3G and LH. However the objectives of the invention are usually achieved by comparison of the signal intensities between tests conducted at different times during the cycle and it is unnecessary to relate this information back to an absolute concentration figure. For this reason within the context of this example, it is convenient to express signals in terms of arbitrary transmission values. A difference in the signal obtained in a different test in the cycle can be expressed as a percentage change in the detected transmission level.

The complete test strip contained within the assay device as depicted in FIG. 6 is represented (not to scale) in FIG. 13. This only shows the basic construction of the test strip. The strip comprises a bibulous sample receiving member 1301 backed with a transparent plastic sheet 1302. The porous part of the sample receiver is made from non-woven fabric, e.g. a polyester/viscous blend. At its left hand end 1303 (as seen in FIG. 13) the porous sample collector overlaps one end 1304 of a strip 609 of porous nitrocellulose also backed with transparent plastic sheet material 1305. Remote from the overlap in the nitrocellulose strip are two deposited lines of reagent 610 and 611 which respectively provide the detection zones for LH and E3G. In the assembled device including the casing (see FIG. 6), these two zones are visible from the exterior. The right hand end 1306 of the sample collector protrudes from the casing and be exposed for sample collection by removal of the cap 601 seen in FIG. 6. At an intermediate location between the overlap end and the exposed end of the sample collector is a region 1307 containing mobilisable particle labelled reagent. This reagent comprises, in excess, two separate populations of particles respectively carrying an anti-LH antibody and an anti-E3G antibody. As depicted in FIG. 13, these two populations have been applied to the same portion of the sample collector, e.g. as a pre-mixture but if desired the two populations can be kept separate and applied to different portions of the collector. Alternatively, one or both of the particle populations can be applied in a region of the nitrocellulose strip. However, for ease of manufacture of the entire device, it is preferable that the particle labelled reagent is deposited in the sample collector. Migration of collected urine sample from the exposed end of the sample collector towards the detection zones will moisten and mobilise the particle labelled reagents and carry them to and beyond the detection zones. Specific binding reactions will cause the build up of particles in the two detection zones, depending on the concentrations of LH and E3G in the applied urine sample. After an appropriate running time for the test, the extent of particle build up in the detection zones can be read using the electronic monitor as described herein. This will provide the monitor with an indication of the concentrations of these two analytes.

Each test device is therefore a combined LH/E3G assay. Examples of the physical construction and methods of manufacture of appropriate devices, including manufacture of reagents, are described in detail in EP-A-291194 and EP-A-383619, EP-A-703454 and EP-A-833160.

A suitable E3G latex is prepared by combining blue-coloured latex particles (mean diameter 380 nm) with an anti-E3G monoclonal antibody of affinity in solution of about $10^{10}$ litres/mole. The antibody (170 ig/ml) is mixed with latex particles (0.5% solids) in a sodium borate buffer at pH 8.5. Vacant binding sites on the latex surface are blocked with BSA (25 mg/ml). The latex is then washed to remove non-adsorbed materials.

A suitable LH latex is prepared from an anti-beta LH monoclonal antibody adsorbed onto blue-coloured latex particles (380 nm). This process is carried out with an antibody to latex ratio of 100 ig/ml to 0.5% solids in a sodium borate buffer (pH 8.5) containing ethanol (ratio of 6 to 1 v/v), followed by blocking the vacant binding sites with BSA (25 mg/ml). The latex is then washed to remove non-adsorbed materials.

An aqueous suspension of equal amounts of both populations of the latex particles as prepared above, 0.008% total solids, in a Tris buffer at pH 8.5 containing 3% BSA and 1% sugar, can be used to deposit these latex populations in the sample receiver.

The solid phase strip on which the levels of E3G and LH are detected is nitrocellulose, of 8 i nominal pore size, bonded to a polyester backing sheet. An E3G-protein (ovalbumen) conjugate, and an anti-alpha LH antibody, are separately plotted as lines onto the nitrocellulose at different locations (respectively represented as 610 and 611 in FIG. 6) using solutions containing 2 mg/ml of the respective reagent in phosphate buffer at pH 7.4. The nitrocellulose is blocked with PVA before being cut into strips.

By way of example only, some appropriate algorithm rules are:

To Identify LH Surge

LH signal greater than 15% T (i.e. 15% drop in transmission).

5% increase over cumulative mean of LH signal.

E3G signal less than 20% T.

No LH surge can be identified before day 9.

To Identify E3G Rise

E3G signal less than 15% T.

Ratio of E3G signal/E3G baseline signal less than 0.65.

Testing Regime

Start on day 6 and continue until ovulation detected, or later.

Start on mean LH surge day minus 7 days.

Fertility Status Display

LOW fertility icon whenever a fertility status is being shown.

HIGH fertility icon if an E3G rise or LH surge day is identified. It can disappear on the third day following detection of LH surge.

PEAK fertility icon on the day when first LH surge day is identified and also on the following day.

It will be appreciated that an algorithm can be put together from a sub-combination of the above rules, several of which are alternatives or can be used to reinforce other rules.

Use can also be made of minimum signals, e.g. E3G signal less than 2% T, to warn of a test device that has failed to run properly for some reason, e.g. inadequate sample quantity.

What is claimed is:

1. A monitoring device for use in conjunction with one or more body fluid testing devices to provide an indication of the time of maximum fertility in the mammalian ovulation cycle, said monitoring device comprising:
   a) a reading means for reading for reading test signals provided by said one or more testing devices, said reading means being operationally connected to said testing devices, said signals including a signal proportional to the concentration of a first analyte in a body fluid, which first analyte exhibits a detectable concentration change at about the time of ovulation in said cycle, and a signal proportional to the concentration of a second analyte in a sample of body fluid, which second analyte exhibits a detectable concentration change after the commencement of said cycle but before the concentration change of said first analyte becomes detectable; and
   b) an electronic processing means for interpreting said test signals obtained in a series of tests conducted following the commencement of said cycle, wherein said electronic processing means of said monitoring device is operationally connected to said reading means, said electronic processing means providing an indication that fertility is elevated when said concentration change of said second analyte has been detected, and an indication that fertility is maximum when said concentration change of said first analyte has been detected.

2. A monitoring device according to claim 1 wherein said first analyte is luteinising hormone (LH).

3. A monitoring device according to claim 1 wherein said second analyte is selected from the group consisting of estradiol and metabolites thereof.

4. A monitoring device according the claim 3 wherein said second analyte is estrone-3-glucuronide (E3G).

5. A monitoring device according to claim 1 wherein said body fluid is urine.

6. A monitoring device according to claim 1 wherein said mammalian ovulation cycle is the human ovulation cycle.

7. A monitoring device according to claim 1 wherein no indication of maximum fertility is provided unless said concentration change of said second analyte has already been detected in the current cycle or is detected no later than the time at which said concentration change of said first analyte is detected.

8. A monitoring device according to claim 1 further comprising a receiving means for receiving said signals from said one or more testing devices said receiving means providing said test signals to said reading means, and a display means for providing said indications of fertility.

9. A monitoring device according to claim 8, wherein said display means includes a visual indication in the form of a bar or similar symbol the height or length of which is altered in either a continuous or step-wise manner as the likelihood of conception increases, attaining a maximum height or length to indicate the most appropriate time in the cycle to attempt conception.

10. A monitoring device according to claim 1 including interface means for communicating with transmitting means for transmitting electronic data.

11. A monitoring device according to claim 10, wherein said transmitting means is a semi-conductor memory device.

12. A test kit comprising a monitoring device according to claim 1 together with at least one body fluid testing device to provide said readable test signals.

13. A test kit comprising a monitoring device according to claim 1 together with a plurality of body fluid testing devices to provide said readable test signals.

14. A test kit according to claim 13 wherein each of said testing devices provides a test signal proportional to said concentration of said first analyte and a test signal proportional to said concentration of said second analyte.

15. A test kit according to 14 wherein each of said test devices uses a single sample of said body fluid.

16. A test kit according to claim 15 wherein said ovulation cycle is the human ovulation cycle, said body fluid is urine, said first analyte is LH and said second analyte is E3G.

17. A method for determining the time of maximum fertility in the human ovulation cycle comprising obtaining samples of body fluid of a human subject, conducting testing over a period of days in the current ovulation cycle on said samples of body fluid to detect an elevated concentration of luteinising hormone (LH) indicative of the event of ovulation and conducting additional testing over a period of days in the current ovulation cycle on additional samples of body fluid obtained from the individual human subject to detect an elevated concentration of an analyte selected form the group consisting of estradiol and metabolites thereof indicative of the imminent event of ovulation.

18. A method according to claim 17, wherein an analyte selected from the group consisting of estradiol and metabolites thereof are detected in the same body fluid samples as is used in the LH tests.

19. A method according to claim 17, or claim 18, wherein an elevated LH concentration apparently indicative of the event of ovulation is disregarded unless an elevated concentration of an analyte selected from the group consisting of estradiol and metabolites thereof has already been detected in the current cycle or is detected concurrently with the elevated LH concentration.

20. A method according to claims 17, or claim 18, wherein a single test is used to determine both LH and said analyte selected from the group consisting of estradiol and metabolites thereof in a single body fluid sample.

21. A test kit for use in a method according to claim 17 comprising:
   a) at least one body fluid testing device that provides a readable signal proportional to the concentration of LH in a sample of said body fluid;
   b) at least one body fluid testing device that provides a readable signal proportional to the concentration of said analyte selected from the group consisting of estradiol and metabolites thereof in a sample of said body fluid;
   c) an electronic monitor having reading means for reading said readable signals and incorporating computer means for interpreting said readable signals and to determine therefrom in conjunction with data from previous body fluid tests whether the event of ovulation in the current cycle is about to occur or has just occurred.

23

22. A test kit according to claim 21, comprising a plurality or testing devices each of which provides a readable signal proportional to said LH concentration and a readable signal proportional to said estradiol/metabolite concentration in a single sample of the body fluid.

23. A test kit according to claim 21, wherein the electronic monitor includes interface means for communicating with a transmitting means for transmitting electronic data.

24. A test kit according to claim 23, wherein said transmitting means is selected from the group consisting of a smart card and a floppy disk.

25. A test kit according to claim 23, wherein said transmitting means is a semi-conductor memory device.

26. A method of patient management comprising testing a patient by analysis of a body fluid of said patient, wherein said analysis is accomplished by:
  (i) providing:
    a) one or more testing devices that provide test signals, including a signal proportional to the concentration of a first analyte in a body fluid, which first analyte exhibits a detectable concentration change at about the time of ovulation in said cycle, and a signal proportional to the concentration of a second analyte in a sample of body fluid, which second analyte exhibits a detectable concentration change after the commencement of said cycle but before the concentration change of said first analyte becomes detectable;
    b) a monitoring device comprising receiving means for receiving one of said one or more testing devices, reading means associated with said receiving means for reading said test signals, electronic processing means for interpreting said test signals, and interface means for communicating with electronic data transmission means; and
    c) electronic data transmission means for transmitting electronic data;
  (ii) downloading electronic data from said monitoring device onto said electronic data transmission means;
  (iii) inputting said downloaded electronic data into said electronic processing means, from which said electronic processing means a health professional thereby derives patient-related information.

27. A method according to claim 26, wherein said electronic data transmission means is a semi-conductor memory device.

28. A method according to claim 26 wherein said first analyte is luteinising hormone (LH).

29. A method according to claim 26 wherein said second analyte is selected from the group consisting of estradiol and metabolites thereof.

30. A method according to claim 29 wherein said second analyte is estrone-3-glucuronide (E3G).

31. A method according to claim 26 wherein said body fluid is urine.

32. A method according to claim 26 wherein said mammalian ovulation cycle is the human ovulation cycle.

33. A method according to claim 26, wherein in response to test signals provided by said one or more testing devices used in a series of tests conducted following the commencement of said cycle, said monitoring device provides an indication that fertility is elevated when said concentration change of said second analyte has been detected, and an indication that fertility is maximum when said concentration change of said first analyte has been detected.

34. A method according to claim 33 wherein no indication of maximum fertility is provided unless said concentration change of said second analyte has already been detected in the current cycle or is detected no later than the time at which said concentration change of said first analyte is detected.

35. A method according to claim 26, wherein said monitoring device includes display means for providing an indication of fertility, said display means including a visual indication in the form of a bar or similar symbol the height or length of which is altered in either a continuous or step-wise manner as the likelihood of conception increases, attaining a maximum height or length to indicate the most appropriate time in the cycle to attempt conception.

36. A method according to claim 26 wherein each of said testing devices provides a test signal proportional to said concentration of said first analyte and a test signal proportional to said concentration of said second analyte.

37. A method according to claim 36 wherein each of said test devices uses a single sample of said body fluid.

38. A method according to claim 26 wherein said ovulation cycle is the human ovulation cycle, said body fluid is urine, said first analyte is LH and said second analyte is E3G.

39. A method according to claim 26 for determining the time of maximum fertility in the mammalian ovulation cycle, wherein testing is conducted over a period of days in the current ovulation cycle on samples of body fluid to detect a change in the concentration of an analyte indicative of the actual event of ovulation and wherein testing is conducted over a period of days in the current ovulation cycle on samples of body fluid to detect a change in the concentration of an analyte indicative of the imminent event of ovulation.

40. A method according to claim 26 for determining the time of maximum fertility in the human ovulation cycle, wherein testing is conducted over a period of days in the current ovulation cycle on samples of body fluid obtained from an individual human subject to detect an elevated concentration of luteinising hormone (LH) indicative of the event of ovulation, wherein additional testing is conducted over a period of days in the current ovulation cycle on samples of body fluid obtained from the individual human subject to detect an elevated concentration of an analyte selected from the group consisting of estradiol and metabolites thereof indicative of the imminent event of ovulation.

41. A method according to claim 40, wherein an analyte selected from the group consisting of estradiol and metabolites thereof are detected in the same body fluid samples as are used in the LH tests.

42. A method according to claim 40 or claim 41 wherein an elevated LH concentration apparently indicative of the event of ovulation is disregarded unless an elevated concentration of an analyte selected from the group consisting of estradiol and metabolites thereof has already been detected in the current cycle or is detected concurrently with the elevated LH concentration.

43. A method according to claim 40 or claim 41, wherein a single test is used to determine both LH and said an analyte selected from the group consisting of estradiol and metabolites thereof in a single body fluid sample.

44. A method according to claim 26, wherein said electronic data transmission means is selected from the group consisting of a smart card and a floppy disk.

45. A method according to claim 26, wherein said electronic data transmission means is interfaced with said monitor to record an event occurring during an ovulation cycle.

46. A method according to claim 45, wherein said event is an act of intercourse.

47. A method according to claim 45, wherein said event is the occurrence of a physiological symptom.

48. A method according to claim 26, wherein said electronic data transmission means is interfaced with said monitoring device to download a result of a specific test for which a specific testing device is provided.

49. A method according to claim 48, wherein said specific test is a test for an analyte selected from the group consisting of human chorionic gonadotrophin (hCG), pregnanediol-3-glucuronide (P3G) and follicle stimulating hormone (FSH).

* * * * *